(12) United States Patent
Lee et al.

(10) Patent No.: US 12,080,195 B2
(45) Date of Patent: Sep. 3, 2024

(54) STRETCHABLE DEVICE SYSTEM AND ELECTRONIC DEVICE

(71) Applicant: Samsung Electronics Co., Ltd., Suwon-si (KR)

(72) Inventors: Gae Hwang Lee, Seongnam-si (KR); Youngjun Yun, Seongnam-si (KR); Jong Won Chung, Hwaseong-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 508 days.

(21) Appl. No.: 17/374,115

(22) Filed: Jul. 13, 2021

(65) Prior Publication Data

US 2022/0101760 A1 Mar. 31, 2022

(30) Foreign Application Priority Data

Sep. 29, 2020 (KR) .......................... 10-2020-0127399

(51) Int. Cl.
*H05K 1/18* (2006.01)
*A61B 5/00* (2006.01)
*A61B 5/0205* (2006.01)
*G09F 9/30* (2006.01)

(52) U.S. Cl.
CPC ............ *G09F 9/301* (2013.01); *A61B 5/0205* (2013.01); *A61B 5/6801* (2013.01); *A61B 2562/18* (2013.01); *A61B 2562/227* (2013.01)

(58) Field of Classification Search
CPC ..... G09F 9/301; A61B 5/0205; A61B 5/6801; A61B 2562/18; A61B 2562/227
USPC ........................................................ 361/749
See application file for complete search history.

(56) References Cited

U.S. PATENT DOCUMENTS

| 9,691,996 | B2 | 6/2017 | Lee | |
|---|---|---|---|---|
| 10,254,499 | B1 * | 4/2019 | Cohen | B29C 64/321 |
| 2012/0165759 | A1 * | 6/2012 | Rogers | A61B 5/6867 |
| | | | | 606/228 |
| 2014/0167006 | A1 | 6/2014 | Kim | |
| 2016/0028153 | A1 * | 1/2016 | Li | H05K 1/142 |
| | | | | 343/718 |
| 2018/0027661 | A1 * | 1/2018 | Ogura | H05K 3/284 |
| | | | | 361/749 |

FOREIGN PATENT DOCUMENTS

| KR | 10-1051634 B1 | 7/2011 |
|---|---|---|
| KR | 10-1097430 B1 | 12/2011 |
| KR | 2014-0077624 A | 6/2014 |
| KR | 10-2015-0077899 A | 7/2015 |
| KR | 2016-0101825 A | 8/2016 |
| KR | 10-2020-0081220 A | 7/2020 |

OTHER PUBLICATIONS

Korean Office Action dated Jul. 5, 2024 issued in corresponding Korean Patent Application No. 10-2020-0127399 and English translation thereof.

* cited by examiner

*Primary Examiner* — Binh B Tran
(74) *Attorney, Agent, or Firm* — Harness, Dickey & Pierce, P.L.C.

(57) ABSTRACT

A stretchable device system includes a stretchable layer having a first elastic modulus, a plurality of unit devices under or on the stretchable layer, and a stretch controlling layer being geometrically stretchable, the stretch controlling layer having a second elastic modulus higher than the first elastic modulus.

21 Claims, 16 Drawing Sheets

STRETCHABLE DEVICE SYSTEM AND ELECTRONIC DEVICE

CROSS-REFERENCE TO RELATED APPLICATION

This application claims priority to and the benefit, under 35 U.S.C. § 119, of Korean Patent Application No. 10-2020-0127399 filed in the Korean Intellectual Property Office on Sep. 29, 2020, the entire contents of which are incorporated herein by reference.

BACKGROUND

1. Field

A stretchable device system and an electronic device are disclosed.

2. Description of the Related Art

In recent years, research on an attachable device directly attaching a display device or a biological device such as a smart skin device, a soft robot, and a biomedical device to an object, a skin of a living-body or clothing has been conducted. Such an attachable device may be required to have stretchability to flexibly respond to shapes of an object or motions of a living body, simultaneously being recovered to its original state.

In order to impart such stretchability, a stretchable layer having high stretchability may be used. However, if the user arbitrarily stretches based on the high stretchability of the stretchable layer, the device may be permanently damaged by exceeding an elastic limit of the device.

SUMMARY

Some example embodiments provide a stretchable device system capable of reducing or preventing damage to devices while securing stretchability.

Some example embodiments provide an electronic device including the stretchable device system.

Some example embodiments provide a protective film for a stretchable device system.

According to some example embodiments, a stretchable device system includes a stretchable layer having a first elastic modulus, a plurality of unit devices under, inside, or on the stretchable layer, and a stretch controlling layer being geometrically stretchable, the stretch controlling layer having a second elastic modulus higher than the first elastic modulus.

The stretch controlling layer may be disposed on, under, or inside the stretchable layer and may be isolated from direct contact with the plurality of unit devices.

The stretch controlling layer may include patterns connected as a whole.

The stretch controlling layer may include geometric lattice patterns.

At least a portion of the stretch controlling layer may have a serpentine or zigzag shape.

The stretch controlling layer may include a plurality of first patterns overlapped with separate, respective unit devices of the plurality of unit devices, and a second pattern connecting adjacent first patterns of the plurality of first patterns.

Each first pattern may have a size covering all edges of a separate unit device of the plurality of unit devices.

The second pattern may include a geometric lattice pattern.

The second pattern may have a serpentine or zigzag shape.

The stretch controlling layer may include a polymer.

The stretchable layer may include a first elastomer having the first elastic modulus, and the stretch controlling layer may include a second elastomer having the second elastic modulus or a non-elastomer having the second elastic modulus.

The first elastomer may include a copolymer including a first structural unit selected from a styrene structural unit, an olefin structural unit, a urethane structural unit, an ether structural unit, and a combination thereof and a second structural unit selected from an ethylene structural unit, a propylene structural unit, a butylene structural unit, an isobutylene structural unit, a butadiene structural unit, an isoprene structural unit, and a combination thereof; polyurethane; polyorganosiloxane; or a combination thereof, and the second elastomer or the non-elastomer may include polystyrene, polyolefin, polyimide, polyamideimide, polyethyleneterephthalate, polyethylenenaphthalate, polymethylmethacrylate, polycarbonate, polyethersulfone, or a combination thereof.

The first elastomer and the second elastomer or the non-elastomer may be a polymer including at least one same structural unit.

The stretchable device system may further include a connecting wire electrically connecting adjacent unit devices of the plurality of unit devices, and at least a portion of the stretch controlling layer may be overlapped with the connecting wire.

The second elastic modulus may be about 10 times to about 1000 times higher than the first elastic modulus.

The first elastic modulus may be greater than or equal to about $10^2$ Pa and less than about $10^8$ Pa, the second elastic modulus may be about $10^8$ Pa to about $10^{10}$ Pa, and the second elastic modulus may be about 10 times higher than the first elastic modulus.

The second elastic modulus may be lower than or equal to an elastic modulus of the plurality of unit devices.

The stretchable layer may include a stretchable substrate supporting the plurality of unit devices, a protective layer or a passivation layer covering the plurality of unit devices, or a combination thereof.

Each unit device may include a light emitting device, a light absorbing device, a transistor, a resistance device, an imaging device, or a combination thereof.

The stretchable device system may be a display panel or a sensor.

According to some example embodiments, an electronic device including the stretchable device system is provided.

According to some example embodiments, a protective film for a stretchable device system includes a stretchable layer including a first elastomer, and a stretch controlling layer under, on, or inside the stretchable layer, the stretch controlling layer including a second elastomer or a non-elastomer having a higher elastic modulus than a separate elastic modulus of the first elastomer, wherein the stretch controlling layer is geometrically stretchable.

The stretch controlling layer may include patterns connected as a whole, and the patterns may include geometric lattice patterns, patterns having a serpentine or zigzag pattern, or a combination thereof.

While securing stretchability, damage to the device may be reduced or prevented.

DETAILED DESCRIPTION

Figure 1:
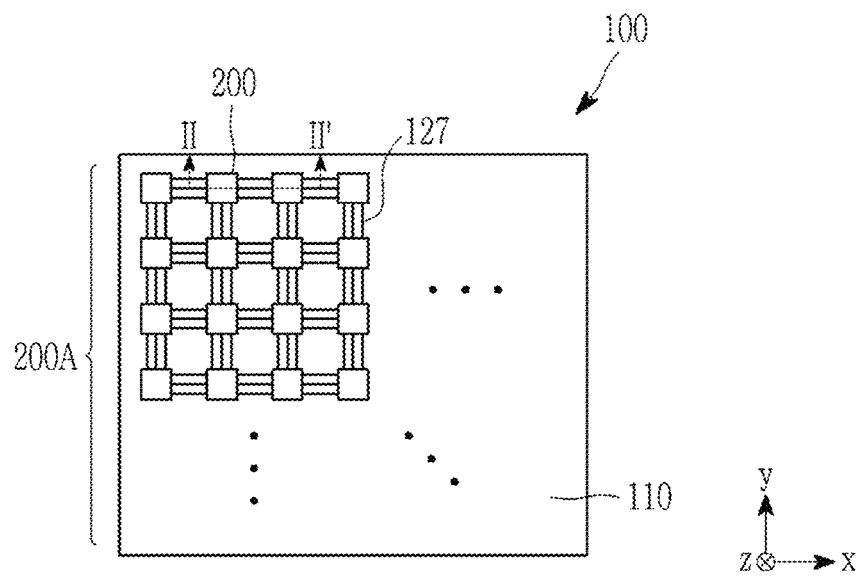
FIG. 1 is a plan view showing an example of an arrangement of unit devices of a stretchable device system according to some example embodiments.

Hereinafter, embodiments will be described in detail so that those of ordinary skill in the art can easily implement them. However, a structure that is actually applied may be implemented in various different forms, and is not limited to the embodiments described herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present (e.g., the element may be isolated from direct contact with the other element). In contrast, when an element is referred to as being "directly on" another element, there are no intervening elements present. It will be understood that when an element such as a layer, film, region, or substrate is referred to as being "on" another element, it may be above or under the other element.

Hereinafter, "combination" includes mixing or a stacked structure of two or more.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%)).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%)).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%)).

It will be understood that elements and/or properties thereof may be recited herein as being "the same" or "equal" as other elements, and it will be further understood that elements and/or properties thereof recited herein as being "the same" as or "equal" to other elements may be "the same" as or "equal" to or "substantially the same" as or "substantially equal" to the other elements and/or properties thereof. Elements and/or properties thereof that are "substantially the same" as or "substantially equal" to other elements and/or properties thereof will be understood to include elements and/or properties thereof that are the same as or equal to the other elements and/or properties thereof within manufacturing tolerances and/or material tolerances. Elements and/or properties thereof that are the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

Hereinafter, a stretchable device system according to some example embodiments will be described.

Figure 2:
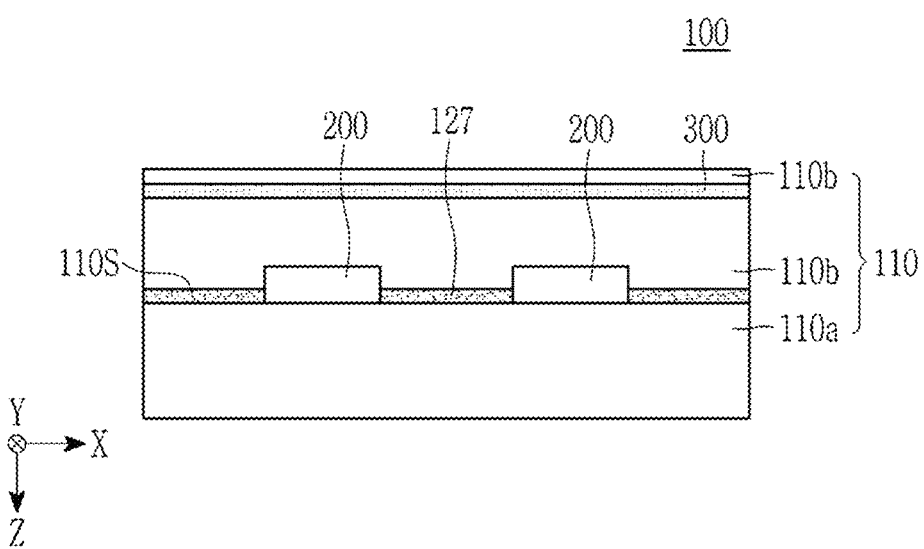
FIG. 2 is a cross-sectional view of the stretchable device system of FIG. 1 taken along line II-II'.

FIG. 1 is a plan view showing an example of an arrangement of unit devices of a stretchable device system according to some example embodiments, and FIG. 2 is a cross-sectional view of the stretchable device system of FIG. 1 taken along line II-II'.

Referring to FIGS. 1 and 2, a stretchable device system 100 according to some example embodiments includes a stretchable layer 110, a plurality of unit devices 200, a connecting wire 127, and a stretch controlling layer 300. In some example embodiments, the stretchable device system 100 and/or the elements thereof may be included in a protective film for a stretchable device system.

The stretchable layer 110 may have stretchability that it may be stretchable in a particular (or, alternatively, predetermined) direction and restored again, and may flexibly respond to external forces or external motions such as twisting, pressing and pulling in a particular (or, alternatively, predetermined) direction.

The stretchable layer 110 may have relatively low stiffness. Herein, the stiffness indicates a degree of resistance to deformation when a force is applied from the outside. Relatively high stiffness may mean that the resistance to deformation is relatively large, so that deformation is small while relatively low stiffness may mean that the resistance to deformation is relatively small, so that the deformation is large. The stiffness may be evaluated from an elastic modulus, and a high elastic modulus may mean high stiffness and a low elastic modulus may mean low stiffness. The elastic modulus may be, for example, a Young's modulus. The stretchable layer 110 may have a relatively low elastic modulus (e.g., first elastic modulus), and the elastic modulus (first elastic modulus) of the stretchable layer 110 may be, for example, less than about $10^8$ Pa, within the range, greater than or equal to about $10^2$ Pa and less than about $10^8$ Pa, about $10^2$ Pa to about $10^7$ Pa or about $10^2$ Pa to about $10^6$ Pa.

The stretchable layer 110 may have a relatively high elongation rate due to a relatively low elastic modulus. Herein, the elongation rate may be a percentage of the length change that is increased to a breaking point with respect to the initial length. The elongation rate of the stretchable layer 110 may be greater than or equal to about 50%, and within the above range, greater than or equal to about 80%, greater than or equal to about 100%, greater than or equal to about 120%, greater than or equal to about 150%, greater than or equal to about 200%, greater than or equal to about 250%, or greater than or equal to about 300%, within the range, about 50% to about 1000%, about 80% to about 1000%, about 100% to about 1000%, about 120% to about 1000%, about 150% to about 1000%, about 200% to about 1000%, about 250% to about 1000%, or about 300% to about 1000%.

The stretchable layer 110 may include an elastomer (e.g., a first elastomer having the first elastic modulus), for example, an organic elastomer, an organic-inorganic elastomer, an inorganic elastomer-like material, or a combination thereof.

The stretchable layer 110 may include, for example, an elastomer including a styrene structural unit, an olefin structural unit, a urethane structural unit, an ether structural unit, an ethylene structural unit, a propylene structural unit, a butylene structural unit, an isobutylene structural unit, a butadiene structural unit, an isoprene structural unit, or a combination thereof; an organosiloxane structural unit; or a combination thereof.

The stretchable layer 110 (e.g., the first elastomer of the stretchable layer 110) may include, for example, a copolymer including a first structural unit selected from a styrene structural unit, an olefin structural unit, a urethane structural unit, an ether structural unit, and a combination thereof, and a second structural unit selected from an ethylene structural unit, a propylene structural unit, a butylene structural unit, and an isobutylene structural unit, a butadiene structural unit, an isoprene structural unit, and a combination thereof; polyurethane; polyorganosiloxane; or a combination thereof.

The stretchable layer 110 may include, for example, a styrene-butadiene rubber (SBR), styrene-ethylene-butylene-styrene (SEBS), styrene-ethylene-propylene-styrene (SEPS), styrene-butadiene-styrene (SBS), styrene-isoprene-styrene (SIS), styrene-isobutylene-styrene (SIBS), polyurethane, polydimethylsiloxane (PDMS), or a combination thereof, but is not limited thereto.

The stretchable layer 110 may include a lower stretchable layer 110a and an upper stretchable layer 110b. The lower stretchable layer 110a may be, for example, a stretchable substrate supporting (e.g., configured to structurally support) the unit devices 200. The upper stretchable layer 110b may be, for example, a stretchable protective layer and/or a stretchable passivation layer covering the unit devices 200 (e.g., overlapping and/or enclosing the unit devices 200). The stretchable layer 110 may thus include the stretchable substrate, the protective layer or passivation layer, or a combination thereof. Accordingly, as shown in FIG. 2, the unit devices 200 may be understood to be under a stretchable layer (e.g., upper stretchable layer 110b), on a stretchable layer (e.g., lower stretchable layer 110a), or inside a stretchable layer (e.g., stretchable layer 110 as a whole).

The unit devices 200 may be arranged on the lower stretchable layer 110a, and may be arranged a long rows and/or columns to form an array 200A. The plurality of unit devices 200 may be arranged in, for example, a Bayer matrix, a PenTile matrix, and/or a diamond matrix, but is not limited thereto.

The plurality of unit devices 200 may be the same as or different from each other, and each unit device 200 may include a light emitting device such as an organic light emitting diode, an inorganic light emitting diode, a quantum dot light emitting diode, a micro light emitting diode, or a perovskite light emitting diode; a light absorbing device such as a photodiode or a photoelectric conversion device; a transistor such as a thin film transistor; a resistance device; an imaging device, or a combination thereof, but is not limited thereto. Each unit device 200 may include a conductor such as an electrode, a semiconductor such as an active layer, an insulator, etc., but is not limited thereto.

For example, each unit device 200 may include a light emitting device that independently displays red light, green light, blue light, or a combination thereof. For example, the light emitting device may include a pair of electrodes and a light emitting layer between the pair of electrodes. The light emitting layer may be configured to emit light in a red wavelength spectrum, a green wavelength spectrum, a blue wavelength spectrum, an infrared wavelength spectrum, or a combination thereof.

For example, each unit device 200 may include a light absorbing device configured to absorb light in a red wavelength spectrum, a green wavelength spectrum, a blue wavelength spectrum, an infrared wavelength spectrum, or a combination thereof. For example, the light absorbing device may include a pair of electrodes and a light absorbing layer between the pair of electrodes. The light absorbing layer may be configured to absorb light in a red wavelength spectrum, a green wavelength spectrum, a blue wavelength spectrum, an infrared wavelength spectrum, or a combination thereof.

As an example, the plurality of unit devices 200 may include a plurality of light emitting devices and a plurality of light absorbing devices alternately arranged along a row and/or column.

For example, each unit device 200 may include one or more thin film transistors. The thin film transistor may include, for example, a switching transistor and/or a driving transistor. The switching transistor may be electrically connected to the gate line and the data line, and may include a first gate electrode connected to the gate line; a first source electrode connected to the data line; a first drain electrode facing the first source electrode; and a first semiconductor which is respectively electrically connected to the first source electrode and the first drain electrode. The driving transistor may include a second gate electrode electrically connected to the first drain electrode; a second source electrode connected to the driving voltage line; a second drain electrode facing the second source electrode; and a second semiconductor which is respectively electrically connected to the second source electrode and the second drain electrode. For example, the first semiconductor and the second semiconductor may each include a semiconductor material and an elastomer. For example, the first semiconductor and the second semiconductor may each include an organic semiconductor material and an elastomer.

In the drawing, although all unit devices 200 are depicted to have the same size, the present inventive concepts are not limited thereto. At least one unit device 200 may be larger or smaller than other unit device 200. In the drawing, although all unit devices 200 are depicted to have the same shape, the present inventive concepts are not limited thereto. At least one unit device 200 may have different shapes from other unit device 200.

The connecting wire 127 may be between adjacent unit devices 200 to electrically connect adjacent unit devices 200. The connecting wire 127 may be one or at least two and arranged along a row direction (e.g., x direction) and a column direction (e.g., y direction) among the unit devices 200 arranged along a raw and/or a column. The connecting wire 127 may be connected to a signal line (not shown), and the signal line may include, for example, a gate line transferring gate signals (or scan signals), a data line transferring data signals, a driving voltage line applying a driving voltage, and/or a common voltage line applying a common voltage, but is not limited thereto.

The connecting wire 127 may include, for example, a low-resistance conductor, and may include silver, gold, copper, aluminum, or an alloy thereof. In the drawings, the connecting wire 127 is illustrated in a straight-line shape for convenience, but is not limited thereto and may have a serpentine or zigzag shape. For example, the connecting wire 127 may have the same shape as at least a portion of the stretch controlling layer 300 to be described later. The connecting wire 127 may be omitted.

The stretch controlling layer 300 may be overlapped with the stretchable layer 110 and separated from (e.g., isolated from direct contact with) the unit devices 200. For example, the stretch controlling layer 300 may be in contact (e.g., direct contact) with at least a portion of the stretchable layer 110. In FIG. 2, an example in which the stretch controlling layer 300 is buried in the upper stretchable layer 110b is illustrated, but the present inventive concepts are not limited thereto, and the stretch controlling layer 300 may be under, on, and/or inside the lower stretchable layer 110a or under, on, and/or inside the upper stretchable layer 110b and may be understood to be on, under, or inside the stretchable layer 110. As shown in FIG. 2, at least a portion of the stretch controlling layer 300 may be overlapped with the connecting wire 127.

As described herein, an element "overlapped" with another element may be overlapped with the other element in a direction extending perpendicular to an upper surface 110S of the lower stretchable layer 110a (e.g., the Z-direction).

The stretch controlling layer 300 may control stretchability of the stretchable device system 100.

The stretchable device system 100 may be required to control not to be stretched in a strain high enough to damage the unit device 200, while it may be flexibly stretched according to the shape of an object or the motion of a living body attached in a particular (or, alternatively, predetermined) strain area. The stretchability of the stretchable device system 100 may be controlled by the stretch controlling layer 300.

The stretch controlling layer 300 may have high stretchability in a particular (or, alternatively, predetermined) stretchable range (strain range), in the same manner as the stretchable layer 110, but when it exceeds a particular (or, alternatively, predetermined) stretchable range, for example, when it exceeds a critical strain, a high stress according to stretching may act on the stretch controlling layer 300, allowing the user to recognize the elastic limit (stretchable limit). Herein, the critical strain of the stretch controlling layer 300 may be determined according to the degree of stretchability of the unit device 200. When the stretchability of the unit device 200 is relatively small, the critical strain of the stretch controlling layer 300 may be relatively low while when the stretchability of the unit device 200 is relatively large, the critical strain of the stretch controlling layer 300 may be relatively high.

The stretchability of the stretch controlling layer 300 may be lower than the stretchability of the stretchable layer 110. Accordingly, when a particular (or, alternatively, predetermined) strain is applied to the stretchable device system 100, the critical strain of the stretch controlling layer 300 is first reached before reaching the critical strain of the stretchable layer 110, so that the user can recognize the elastic limit, and thus, damage to the unit device 200 due to excessive stretching may be reduced or prevented. That is, the critical strain of the stretchable device system 100 may be determined by the critical strain of the stretch controlling layer 300.

If there is no stretch controlling layer 300, the stretchability of the stretchable device system 100 may be determined by the stretchable layer 110 having high stretchability. When the user arbitrarily stretches the stretchable device system 100 based on the high stretchability of the stretchable layer 110, the unit device 200 may be permanently damaged after removing the stretching due to excess of the elastic limit of the unit device 200. The stretch controlling layer 300 may reduce or prevent damage to the unit device 200 in advance by allowing the user to recognize the elastic limit.

The stretch controlling layer 300 may have a geometrically stretchable structure, while when it is structurally completely stretched, it has a high elastic modulus so that it is no longer stretched beyond a critical strain. For example, where the stretchable layer 110 is understood to have a first elastic modulus as described above, the stretch controlling layer 300 may be understood to have a second elastic modulus that is higher than the first elastic modulus of the stretchable layer 110. Accordingly, the stretch controlling layer 300 may be understood to be geometrically stretchable. As described above, the stretch controlling layer 300 may have high stretchability at a particular (or, alternatively, predetermined) stretchable range (strain range), and when it exceeds a particular (or, alternatively, predetermined) stretchable range, high stress may be applied.

First, the stretch controlling layer 300 may have a geometrically stretchable structure in a particular (or, alternatively, predetermined) stretchable range. The geometrically stretchable structure may provide the same level of stretchability as the stretchable layer 110 in a particular (or, alternatively, predetermined) stretchable range without disturbing the stretchability of the stretchable device system 100. In some example embodiments, the geometrically stretchable structure cannot be stretched any more when it is completely stretched (relaxed). For example, the geometrically stretchable structure may provide stretchability while being easily stretched in a particular (or, alternatively, predetermined) stretchable range, and may no longer be stretched when it exceeds the stretchable range. The geometrically stretchable structure may be a structure that can be stretched by structural deformation due to stretching, and may include lines and/or patterns that are connected as a whole. Accordingly, the stretch controlling layer 300 may be understood to comprise patterns connected as a whole.

Figure 3:
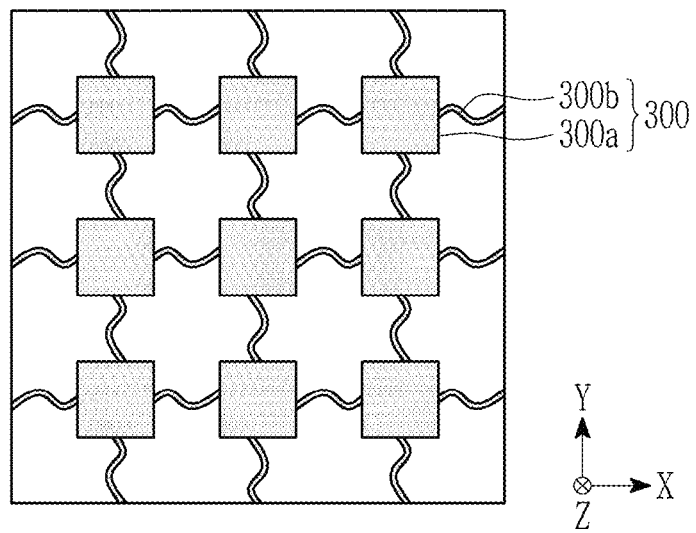
FIG. 3 is a plan view showing an example of a geometrically stretchable structure of a stretch controlling layer applied to the stretchable device system of FIG. 1, FIGS. 4A, 4B, and 4C are schematic views showing examples of patterns having serpentine or zigzag patterns in a geometrically stretchable structure of the stretch controlling layer of FIG. 3, FIGS. 5 and 6 are plan views showing examples of geometric patterns of a stretch controlling layer applied to the stretchable device system of FIG. 1.
Figure 4A:
Figure 4B:
Figure 4C:
Figure 5:
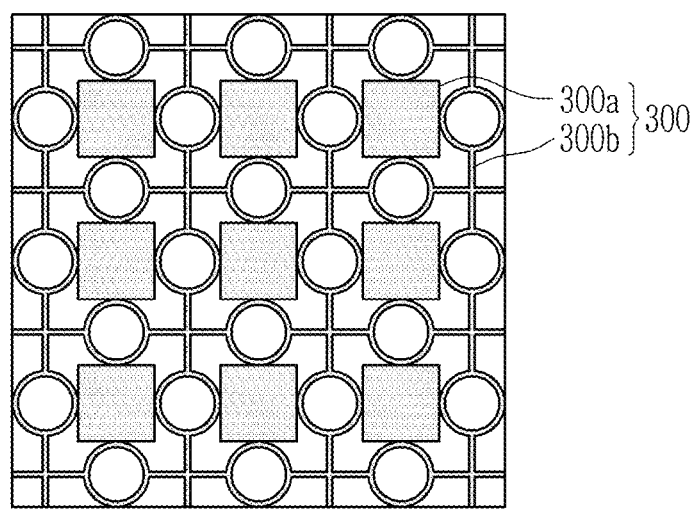
Figure 6:
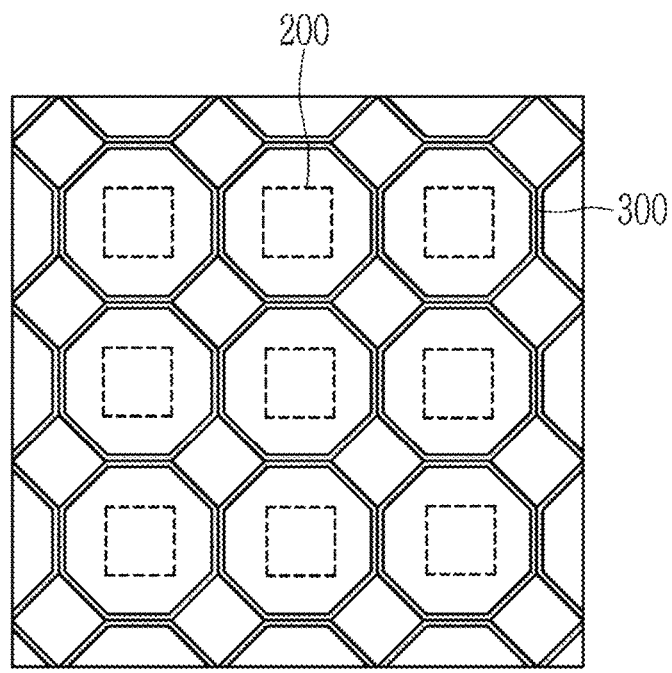
Figure 7:
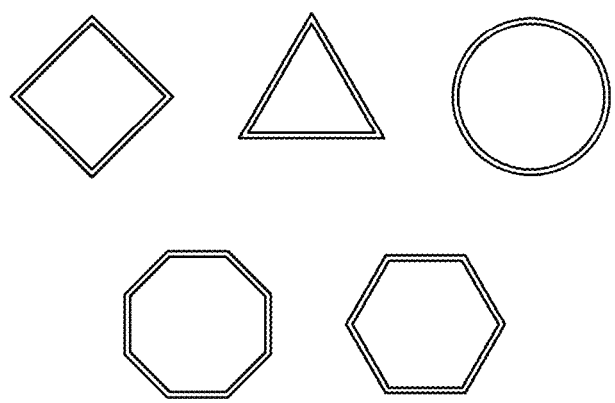
FIG. 7 is a schematic view showing examples of various figures in the geometrical stretchable pattern of the stretch controlling layer of FIGS. 5 and 6.

FIG. 3 is a plan view showing an example of a geometrically stretchable structure of a stretch controlling layer applied to the stretchable device system of FIG. 1, FIGS. 4A to 4C are schematic views showing examples of patterns having serpentine or zigzag patterns in a geometrically stretchable structure of the stretch controlling layer of FIG. 3, FIGS. 5 and 6 are plan views showing examples of geometric patterns of a stretch controlling layer applied to the stretchable device system of FIG. 1, and FIG. 7 is a schematic view showing examples of various figures in the geometrical stretchable pattern of the stretch controlling layer of FIGS. 5 and 6.

Referring to FIGS. 3 and 4A to 4C, a geometrically stretchable structure (e.g., at least a portion of the stretch controlling layer 300) may have a serpentine or zigzag shape. For example, the serpentine or zigzag lines may be a half circle (FIG. 4A), a sinusoidal (FIG. 4B), a zigzag shape (FIG. 4C), or a combination thereof, but limited thereto. Such a serpentine or zigzag shape may provide flexibility to the stretch controlling layer 300 during stretching.

Referring to FIG. 3 with FIG. 1, the geometrically stretchable structure may include a first pattern 300a respectively overlapped with a plurality of unit devices 200 and a second pattern 300b between the first pattern 300a and its adjacent first patterns 300a. Restated, the stretch controlling layer 300 may include a plurality of first patterns 300a overlapped in the direction extending perpendicular to the upper surface 110S of the lower stretchable layer 110a (e.g., the Z-direction) with separate respective unit devices of the unit devices 200, and a second pattern 300b connecting adjacent first patterns 300a of the plurality of first patterns 300a. The first pattern 300a may have a sufficient size covering all the edges of the corresponding unit device 200 and accordingly, effectively reduce or prevent a strain focused on the edges of the unit devices 200. Restated, each first pattern 300a may have a size covering all edges of a separate unit device 200 such that the first pattern 300a completely overlaps the entire unit device 200 in the Z-direction. The second pattern 300b may comprise geometric lattice patterns. The second pattern 300b may have the aforementioned serpentine or zigzag shape, for example, shapes shown in FIGS. 4A to 4C. The second pattern 300b may be overlapped with the connecting wire 127, for example, have the same plane shape as that of the connecting wire 127.

Referring to FIGS. 5 to 7, the geometrically stretchable structure (e.g., the stretch controlling layer 300, for example the first patterns 300a and/or the second pattern 300b) may include geometric lattice patterns. The geometric lattice patterns may include a lattice, a shape (a circle, and/or a polygon), or a combination thereof, which is repeatedly disposed in the whole surface of the stretch controlling layer 300. The patterns of the stretch controlling layer 300 may be connected as a whole, for example as shown in at least FIG. 6.

For example, referring to FIGS. 5 and 7, the geometric lattice patterns may have a structure that first lines extending in the first direction and second lines extending in the second direction are crossed each other, and particular (or, alternatively, predetermined) shapes (a circle, and/or a polygon) providing the first lines and/or the second lines with flexibility are disposed. The first direction and the second direction may be, for example, perpendicular. The shapes, as shown in FIG. 7, may be hollow circles or hollow polygons and provide flexibility to the stretch controlling layer 300, when stretched in a particular (or, alternatively, predetermined) direction.

Referring to FIG. 5 with FIG. 1, the geometrically stretchable structure may include the first pattern 300a overlapped with each of the plurality of unit devices 200 and the second patterns 300b connecting between one first pattern 300a with its adjacent first pattern 300a. The first pattern 300a may have a sufficient size covering all the edges of the unit device 200 and accordingly, effectively reduce or prevent a strain focused on the edges of the unit device 200. The second pattern 300b may be the aforementioned geometric lattice pattern.

For example, referring to FIGS. 6 and 7, the geometric lattice patterns may have a structure that lines in all directions are arranged and linked with the particular (or, alternatively, predetermined) shape providing flexibility to the stretch controlling layer 300. The shape, as shown in FIG. 7, may be a hollow circle or a hollow polygon and provide flexibility to the stretch controlling layer 300, when stretched in a particular (or, alternatively, predetermined) direction. Referring to FIG. 6, the geometrically stretchable structure may be disposed between the adjacent unit devices 200.

In some example embodiments, the stretch controlling layer 300 may have a higher elastic modulus than the stretchable layer 110. Accordingly, when the stretch controlling layer 300 is stretched to exceed the stretchable range of the geometrically stretchable structure, the high elastic modulus of the stretch controlling layer 300 puts a high stress on a user, so that the user may recognize an elastic limit and thus control additional stretching.

The elastic modulus of the stretch controlling layer 300 (e.g., the second elastic modulus) may be greater than or equal to about 10 times as high as that of the stretchable layer 110 (e.g., the first elastic modulus of the stretchable layer 110), and within the range, greater than or equal to about 50 times, greater than or equal to about 100 times, greater than or equal to about 200 times, or greater than or equal to about 300 times, or about 10 times to about 1000 times, about 50 times to about 1000 times, about 100 times to about 1000 times, about 200 times to about 1000 times, or about 300 times to about 1000 times. In addition, the elastic modulus of the stretch controlling layer 300 (e.g., second elastic modulus) may be lower than that (e.g., an elastic modulus) of each of the unit devices 200 (e.g., an elastic modulus of the unit devices 200). The elastic modulus (second elastic modulus) of the stretch controlling layer 300 may be, for example, greater than or equal to about $10^8$ Pa, and within the range, greater than or equal to about $5 \times 10^8$ Pa or greater than or equal to about $10^9$ Pa, about $10^8$ Pa to about $10^{10}$ Pa, about $5 \times 10^8$ Pa to about $10^{10}$ Pa, or about $10^9$ Pa to about $10^{10}$ Pa.

The stretch controlling layer 300 may include an elastomer or a non-elastomer having an elastic modulus higher than that of the elastomer included in the stretchable layer 110. Restated, for example, the stretchable layer 110 may include a first elastomer having the first elastic modulus of the stretchable layer 110, and the stretch controlling layer 300 may include a second elastomer having the second elastic modulus of the stretch controlling layer 300 or a non-elastomer having the second elastic modulus. The stretch controlling layer 300 (e.g., the second elastomer or the non-elastomer of the stretch controlling layer 300) may include, for example, a polymer, for example, polystyrene, polyolefin, polyimide, polyamideimide, polyethylene terephthalate, polyethylene naphthalate, polymethyl methacrylate, polycarbonate, polyether sulfone, or a combination thereof. Alternatively, the stretch controlling layer 300 may include an elastomer included in the aforementioned stretchable layer 110, such as a high elastic modulus polymer obtained by adding a high content of a curing agent and/or a multifunctional curing agent upon curing of a styrene-butadiene rubber (SBR), styrene-ethylene-butylene-styrene (SEBS), styrene-ethylene-propylene-styrene (SEPS), styrene-butadiene-styrene (SBS), styrene-isoprene-styrene (SIS), styrene-isobutylene-styrene (SIBS), polyurethane, polydimethylsiloxane (PDMS), or a combination thereof, but is not limited thereto. Herein, the multifunctional curing agent may have a plurality of functional groups, for example, 4 or more, 6 or more, or 8 or more functional groups.

For example, the stretchable layer 110 and the stretch controlling layer 300 may include at least one structural unit in common (e.g., the first elastomer and the second elastomer or non-elastomer may include at least one same structural unit), for example, a styrene structural unit, an olefin structural unit, a urethane structural unit, an ether structural unit, or a combination thereof, in common. Accordingly, it is possible to effectively reduce or prevent the stretch controlling layer 300 from being separated or detached from the stretchable layer 110 by improving adhesion between the stretchable layer 110 and the stretch controlling layer 300. For example, the stretchable layer 110 and the stretch controlling layer 300 may include a styrene structural unit in common. The stretchable layer 110 may include, for example, a styrene-butadiene rubber (SBR), styrene-ethylene-butylene-styrene (SEBS), styrene-ethylene-propylene-styrene (SEPS), styrene-butadiene-styrene (SBS), styrene-isoprene-styrene (SIS), styrene-isobutylene-styrene (SIBS) or a combination thereof, and the stretch controlling layer 300 may include polystyrene.

In this way, the stretch controlling layer 300 may provide stretchability within a particular (or, alternatively, predetermined) stretchable range due to the geometrically stretchable structure and the high elastic modulus, and simultaneously, make a user recognize an elastic limit due to a high stress according to the stretching, when stretched beyond the particular (or, alternatively, predetermined) stretchable range. Accordingly, the stretch controlling layer 300 may first reach a critical strain before the stretchable layer 110 reaches a critical strain, and thus control stretching of the stretchable device system 100 and reduce or prevent a damage of the unit device 200 due to the excessive stretching.

Figure 8:
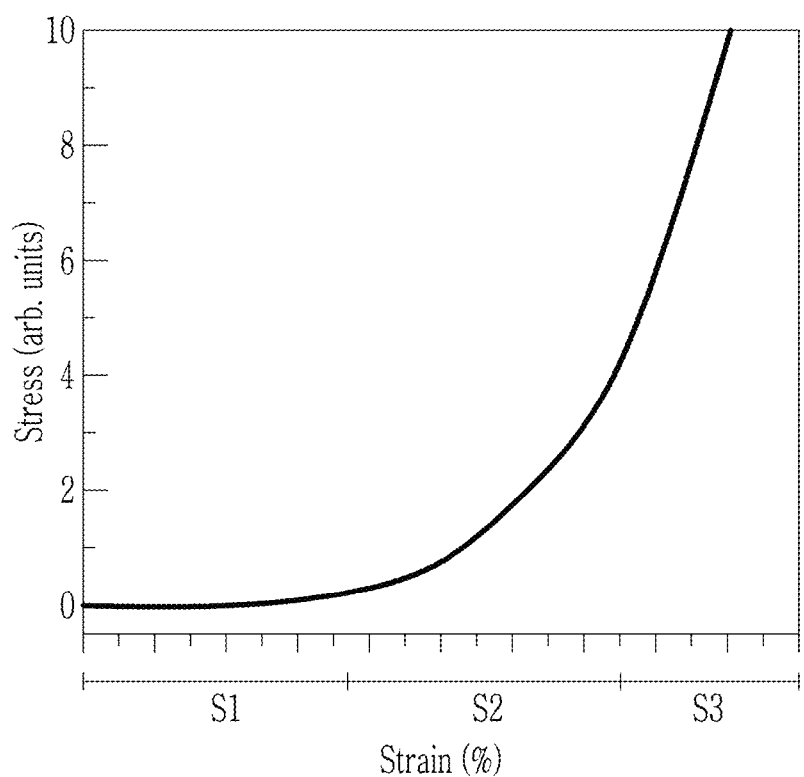
FIG. 8 is a strain-stress graph according to an example of the stretchable device system of FIG. 1.

FIG. 8 is a strain-stress graph according to an example of the stretchable device system of FIG. 1.

Referring to FIG. 8, a strain-stress curve of the stretchable device system 100 may have a first strain section S1 where a stress is constant or very gently increases according to a strain increase due to stretching of the stretchable layer 110, a second strain section S2 where the stress gradually increases according to the strain increase due to the deformation of the geometric structure of the stretch controlling layer 300, and a third strain section S3 where an elastic limit is recognized due to a very high stress according to the stretching due to the high elastic modulus of the stretch controlling layer 300. The stretchable device system 100 may show this strain-stress curve due to the stretch controlling layer 300 and thus may effectively recognize the elastic limit as well as secure stretchability.

In some example embodiments, in some of the aforementioned example embodiments, an example of the stretchable device system 100 equipped with the stretch controlling layer 300 is illustrated, but the present inventive concepts are not limited thereto. The stretch controlling layer 300 may be independently disposed and thus, attached to and detached from the stretchable device system 100. Accordingly, the stretch controlling layer 300 may be separated from the stretchable device system 100 and so, independently used. For example, the stretch controlling layer 300 may be included in a protective film to recognize the elastic limit of the stretchable device system 100, and the protective film may include, for example, a stretchable layer and a stretch controlling layer under, on, or inside the stretchable layer. The stretchable layer and the stretch controlling layer are the same as described above, respectively.

The aforementioned stretchable device system 100 may be, for example, a display panel or a sensor requiring stretchability. The stretchable device system 100 may include, for example, a bendable display panel, a foldable display panel, a rollable display panel, a wearable device, and a skin-like display panel, a skin-like sensor, a large-area conformable display, smart clothing, etc., but the present inventive concepts are not limited thereto.

For example, the aforementioned stretchable device system 100 may be included in a skin-like display panel.

Figure 9:
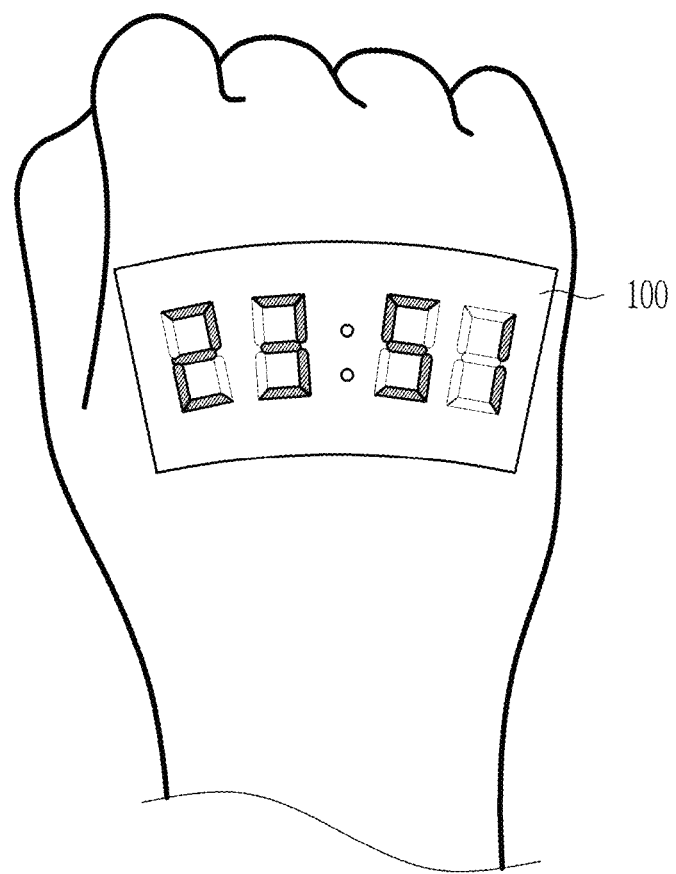
FIG. 9 is a schematic view showing an example of a skin-like display panel.
Figure 10A:
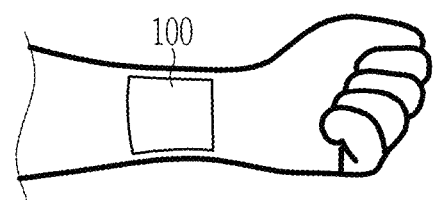
FIGS. 10A, 10B, 10C, and 11 are schematic views showing examples of biometric sensors.
Figure 10B:
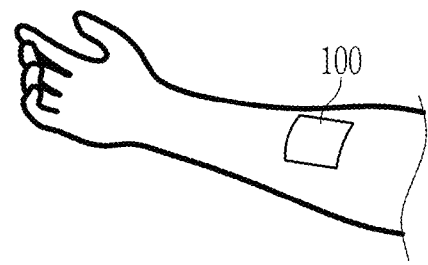
Figure 10C:
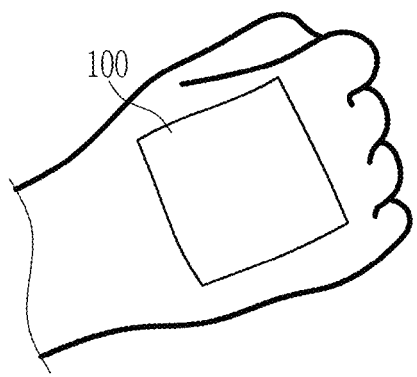

FIG. 9 is a schematic view showing an example of a skin-like display panel.

The stretchable device system 100 may be a skin-like display panel, which is an ultrathin display panel, and may be attached to a part of a living body such as a hand. The skin-like display panel may display particular (or, alternatively, predetermined) information such as various letters and/or images. The skin-like display panel may include, for example, a light emitting device such as an inorganic light emitting diode, a micro light emitting diode, an organic light emitting diode, a quantum dot light emitting diode, or a perovskite light emitting diode as the aforementioned unit device 200, but is not limited thereto.

For example, the aforementioned stretchable device system 100 may be may be a sensor such as a biometric sensor.

FIGS. 10A to 10C and 11 are schematic views showing examples of biometric sensors.

The stretchable device system 100 may be an attachable biometric sensor, and is attached to a living body surface such as skin, an internal body such as an organ, or an indirect means contacting a living body such as clothing to detect and measure biometric information such as a biometric signal. For example, a biometric sensor may be an electroencephalogram (EEG) sensor, an electrocardiogram (ECG) sensor, a blood pressure (BP) sensor, an electromyography (EMG) sensor, a diabetes (blood glucose, BG) sensor, a light blood flow photoplethysmography (PPG) sensor, an accelerometer, a RFID antenna, an inertial sensor, an activity sensor, a strain sensor, a motion sensor, or a combination thereof, but is not limited thereto. The biometric sensor is attached to the living body in an ultrathin patch typed biometric sensor or band typed biometric sensor, so that biometric information may be monitored in real time.

Figure 11:
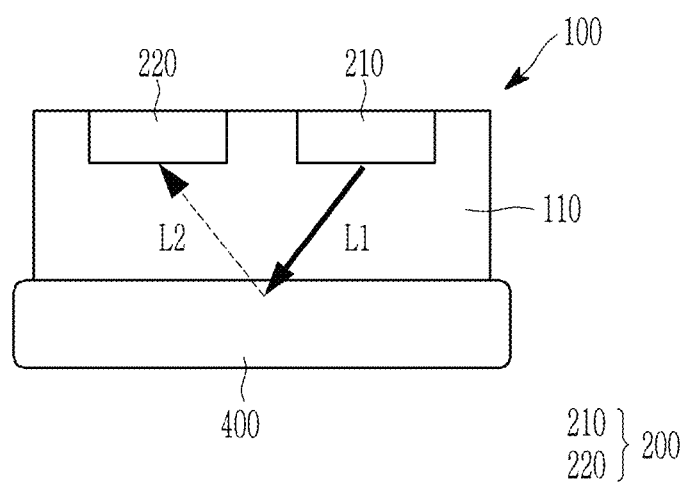

Referring to FIG. 11, the stretchable device system 100 may include a photoplethysmography (PPG) sensor, and the photoplethysmography (PPG) sensor may include the light emitting device 210 and the light absorbing device 220 as the aforementioned unit device 200.

The light emitting device 210 may be configured to emit first light L1 for detecting a biosignal. The light emitting device 210 may be, for example, an infrared light emitting diode configured to emit first light L1 in an infrared wavelength spectrum and/or a visible light emitting diode configured to emit first light L1 in a visible light wavelength spectrum. The first light L1 emitted from the light emitting device 210 may be reflected by an object 400 (e.g., a living body such as skin or blood vessels) or absorbed in the object 400.

The light absorbing device 220 may be configured to absorb second light L2 reflected by the object 400 from the first light L1 emitted from the light emitting device 210 and convert the second light L2 into an electrical signal. The electrical signal converted from the reflected second light L2 may include biometric information such as heart rate, oxygen saturation, stress, arrhythmia, and blood pressure. The electrical signal including the biometric information may be transferred into a sensor IC (not shown) or a processor (not shown).

For example, the stretchable device system 100 may be an electromyography (EMG) sensor or a strain sensor attached to a joint for a rehabilitation treatment of patients with joint and muscle problems. The electromyography (EMG) sensor or the strain sensor may be attached to an area requiring the treatment and thus secure data necessary for the rehabilitation by quantitatively measuring motions of muscles or joints.

The aforementioned stretchable device system such as a display panel and/or a sensor may be included in various electronic devices, and the electronic device may further include a processor (not shown) and a memory (not shown). The electronic device may be a mobile; TV; a health care device, and the like, and the health care device may be, for example, a photoplethysmography (PPG) sensor, an electroencephalogram (EEG) sensor, an electrocardiogram (ECG) sensor, a blood pressure (BP) sensor, an electromyography (EMG) sensor, a blood glucose (BG) sensor, an accelerometer device, a RFID antenna device, an inertial sensor, an activity sensor, a strain sensor, a motion sensor, or a combination thereof, but is not limited thereto.

Figure 12:
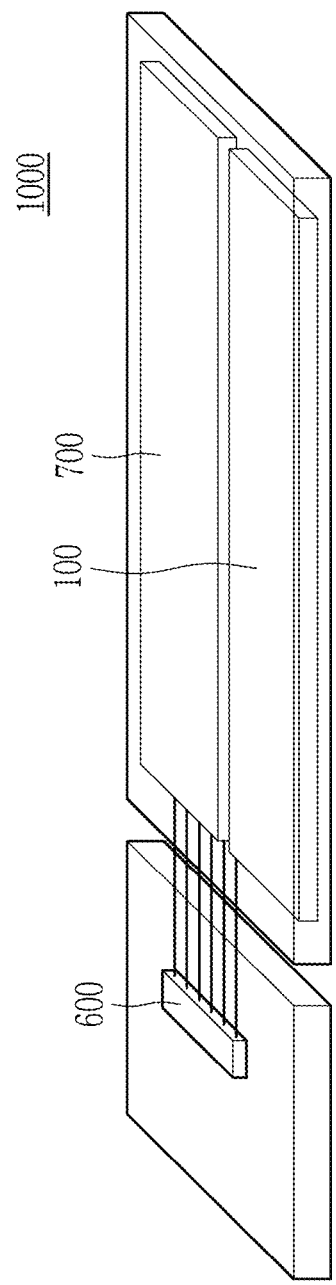
FIG. 12 is a schematic view showing an example of a health care device according to some example embodiments.

FIG. 12 is a schematic view showing an example of a health care device according to some example embodiments.

Referring to FIG. 12, the health care device 1000 (e.g., an electronic device) according to some example embodiments may be a patch-typed or band-typed attachable heath care device and include the aforementioned stretchable device system 100; an IC sensor and/or a processor 600 for processing biometric signals obtained from the stretchable device system 100, and a display area 700 (e.g., a display device, such as an organic light emitting diode (OLED) display screen) for displaying the obtained biometric signals into various letters and/or images.

In some example embodiments, some or all of the devices and/or elements thereof as described herein with reference to any of the drawings (including without limitation the elements of the health care device 1000, the IC sensor and/or a processor 600, the display area 700, the stretchable device system 100, or the like) may include, may be included in, and/or may be implemented by one or more instances of processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), an application processor (AP), a microcomputer, a field programmable gate array (FPGA), and programmable logic unit, a microprocessor, application-specific integrated circuit (ASIC), a neural network processing unit (NPU), an Electronic Control Unit (ECU), and the like. In some example embodiments, the processing circuitry may include a non-transitory computer readable storage device, for example a solid state drive (SSD), storing a program of instructions, and a processor (e.g., CPU) configured to execute the program of instructions to implement the functionality of any of the elements of the devices and/or elements thereof as described herein (including without limitation some or all of the health care device 1000 shown in FIG. 12).

Hereinafter, some example embodiments are illustrated in more detail with reference to examples. However, the present scope off the inventive concepts are not limited to these examples.

Optical Simulation I

Examples 1 to 3

Strain-stress responses according to the geometrically stretchable structures are evaluated.

The strain-stress responses are evaluated from a mechanical simulation using a COMSOL Multiphysics software with assuming a structure that a stretch controlling layer (the geometrically stretchable structures shown in FIGS. 4A to 4C) is inserted into a stretchable layer (200 μm×200 μm).

It is set as follows.

Elastic modulus (Young's Modulus) of stretchable layer: $13 \times 10^6$ Pa

Elastic modulus (Young's Modulus) of stretch controlling layer: $2.5 \times 10^9$ Pa Poisson ratio: 0.35, Density: 1200 kg/m³, Thickness: 1 μm, Shape: FIG. 4A (half circle) (Example 1), FIG. 4B (sinusoidal) (Example 2), and FIG. 4C (rectangular) (Example 3).

Figure 13:
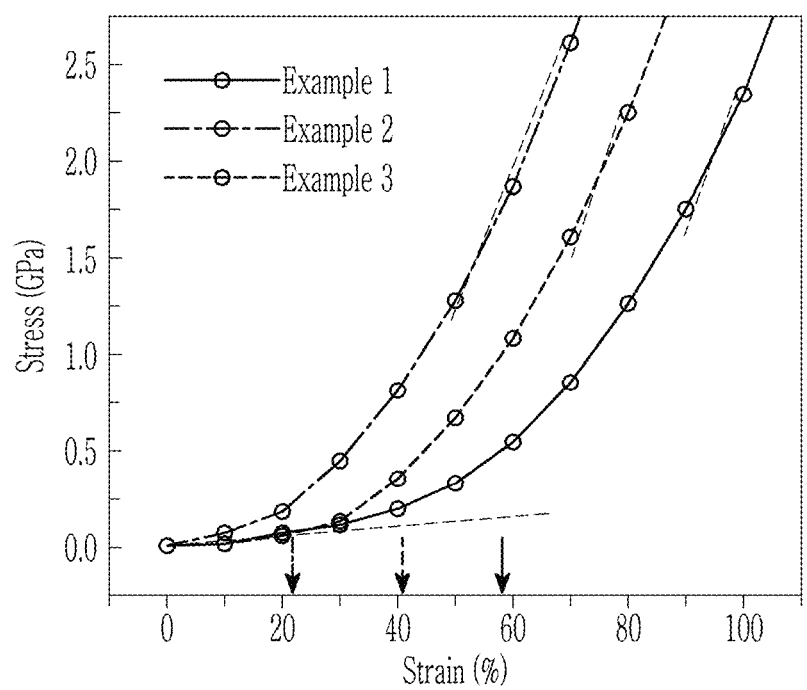
FIG. 13 is a strain-stress graph of a geometrically stretchable structure according to Examples 1 to 3.

The results are shown in FIG. 13 and Table 1.

FIG. 13 is a strain-stress graph of the geometrically stretchable structures according to Examples 1 to 3.

TABLE 1

| | Geometric maximum strain (%) | Length:thickness ratio (@critical strain) |
|---|---|---|
| Example 1 | 57 | 6.2:1 |
| Example 2 | 22 | 6.0:1 |
| Example 3 | 41 | 6.1:1 |

The geometric maximum strains (geometric max strain) in Table 1 are obtained by dividing a total geometric length depending on a shape by a width of a structure, which tells how much the structures are twisted. The patterns shown in FIGS. 4A to 4C all have the same width but a different geometric length depending on the shape.

In addition, referring to FIG. 13, in the geometrically stretchable structures according to Examples 1 to 3, a stress slope rapidly changes, as a strain increases, and around the geometric maximum strain in Table 1, the strain-stress slope sharply increases. In FIG. 13, the geometric maximum strains (indicated by arrows) where the slopes sharply increase varies depending on the shapes of the geometrically stretchable structures, but the saturated strain-stress slopes (marked by a dotted line) are all the same, because a material having the same elastic modulus is assumed.

Optical Simulation II

Examples 4 to 7

Strain-stress responses of the geometrically stretchable structures depending on an elastic modulus are evaluated.

The strain-stress responses of the geometrically stretchable structures depending on an elastic modulus are evaluated from a mechanical simulation using a COMSOL Multiphysics software with assuming a structure that a stretch controlling layer (a geometrically stretchable structure shown in FIG. 4C) is inserted into a stretchable layer (200 μm×200 μm).

It is set as follows.
Elastic modulus (Young's Modulus) of stretchable layer: $13 \times 10^6$ Pa
Elastic modulus (Young's Modulus) of stretch controlling layer (geometrically stretchable structure): $0.1 \times 10^9$ Pa (Example 4), $1 \times 10^9$ Pa (Example 5), $2.5 \times 10^9$ Pa (Example 6), $1.0 \times 10^{10}$ Pa (Example 7)
Poisson ratio: 0.35,
Density: 1200 kg/m$^3$
Thickness: 1 μm
Length: sphere
Shape: FIG. 4C
The results are shown in FIG. 14.

Figure 14:
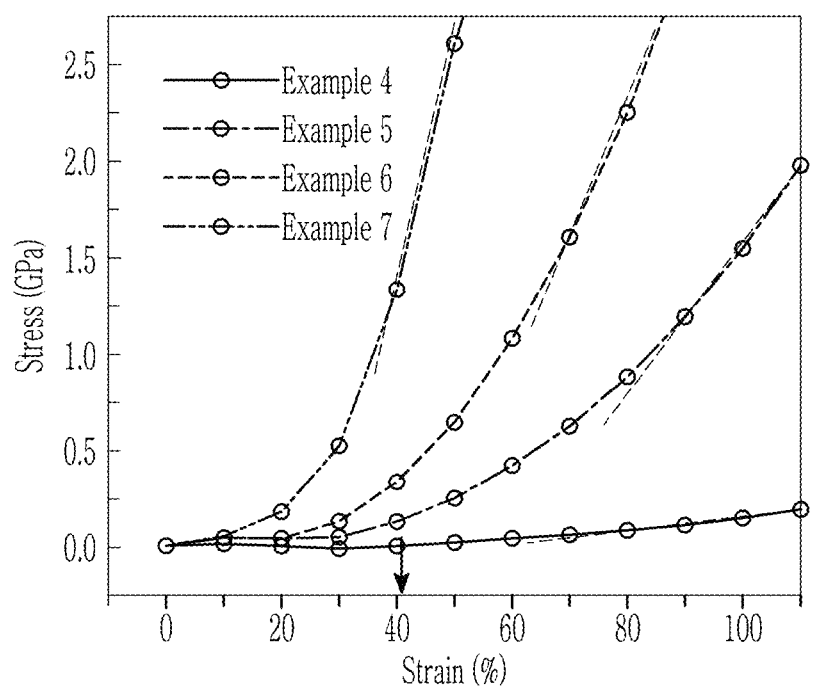
FIG. 14 is a strain-stress graph according to the elastic modulus of a geometrically stretchable structure.

FIG. 14 is a strain-stress graph according to the elastic modulus of a geometrically stretchable structure according to Examples 4 to 7.

Referring to FIG. 14, the geometrically stretchable structures according to Examples 4 to 7 exhibit that a stress slope rapidly changes according to a strain increase. In FIG. 14, since the geometrically stretchable structures are assumed to use a material having a different elastic modulus, saturated strain-stress slopes (marked by dotted lines) depending on an elastic modulus are different each other. In some example embodiments, since the geometrically stretchable structures are assumed to have the same shape, the geometrically stretchable structures according to Examples 4 to 7 have the same geometric maximum strain (indicated by arrows) where the slopes sharply increase.

Manufacture of Stretchable Device System I

Example 8

On a glass substrate coated with a sacrificial layer, a 4.5 μm-thick lower stretchable layer (a stretching ratio: 700%, an elastic modulus: ~1 MPa) is formed by coating a solution in which styrene-ethylene-butylene-styrene (SEBS) including a styrene structural unit and an ethylene/butylene structural unit in a ratio of 20:80 (w/w) (H1052, Asahi Kasei) and a hardener in toluene and then, drying, curing, and patterning it. Subsequently, on the lower stretchable layer, a polyimide precursor solution is coated and treated through photolithography to form a stretch controlling layer including a 10 μm-thick serpentine-shaped polyimide pattern (an elastic modulus: about 2.5 GPa). On the stretch controlling layer, a solution prepared by dissolving styrene-ethylene-butylene-styrene (SEBS) (H1052, Asahi Kasei) and a hardener in toluene is coated, dried, cured, and patterned to form a 10 μm-thick stretchable layer (a stretching ratio: about 20%, an elastic modulus: about 80 MPa), manufacturing a stretchable device system.

Evaluation I

Figure 15:
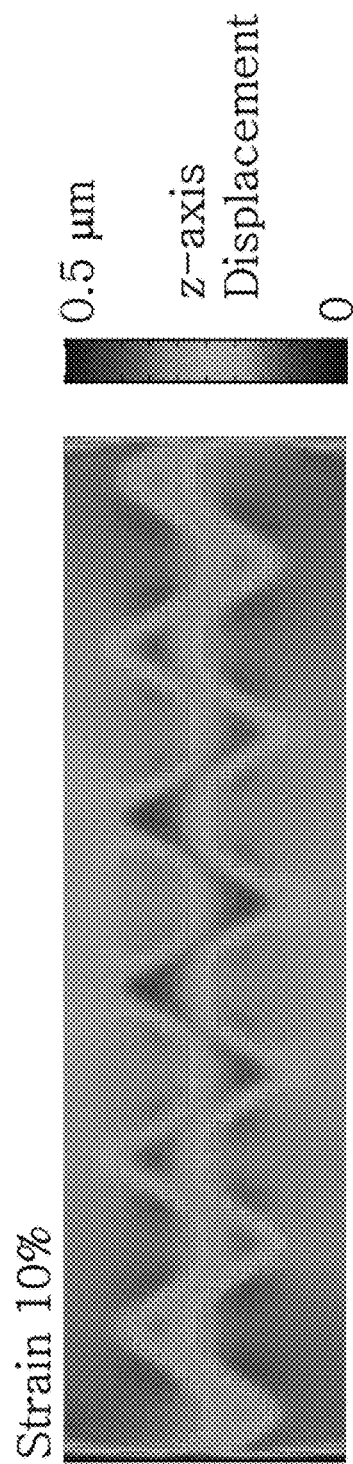
FIG. 15 is a simulation image of a change in the z-axis shape when the stretchable device system according to Example 8 is stretched with 10% strain.
Figure 16:
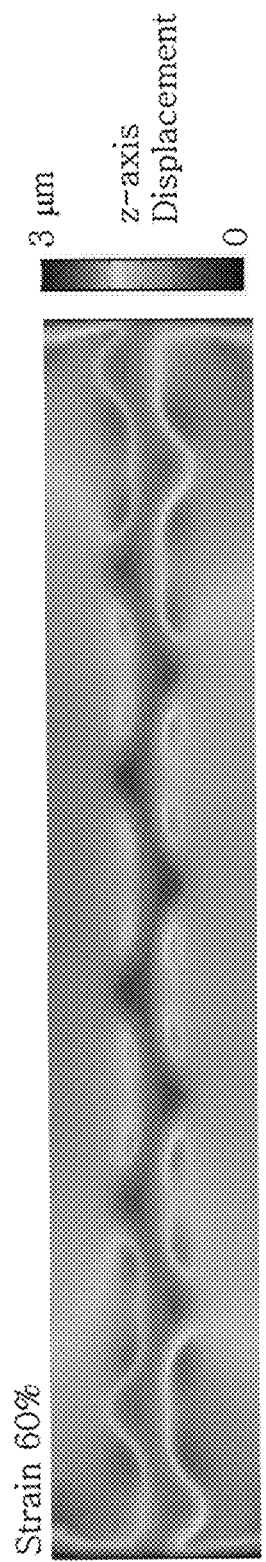
FIG. 16 is a simulation image of a change in the z-axis shape when the stretchable device system according to Example 8 is stretched with 60% strain.

FIG. 15 is a simulation image of a change in the z-axis shape when the stretchable device system according to Example 8 is stretched with 10% strain, and FIG. 16 is a simulation image of a change in the z-axis shape when the stretchable device system according to Example 8 is stretched with 60% strain.

Referring to FIG. 15, the geometrically stretchable structure on the in-plane is distorted in a z axis direction, when strained by stretching. In addition, referring to FIG. 16, even if 60% strain is applied to the geometrically stretchable structure formed on the in-plane, the z axis is shifted about 3 μm, which is sufficiently smaller than a thickness of the stretchable layer (stretchable substrate). Accordingly, even when a significant amount of strain is applied to the geometrically stretchable structure, there may be no problem with the operation of the stretchable device system.

Manufacture of Stretchable Device System II

Example 9

A solution prepared by dissolving styrene-ethylene-butylene-styrene (SEBS) including a styrene structural unit and an ethylene/butylene structural unit in a ratio of 67:33 (w/w) (H1043, Asahi Kasei) and a hardener in toluene is coated on a glass substrate coated with a sacrificial layer, and then dried, cured, and patterned to form a 3 μm-thick lower stretchable layer (a stretching ratio: about 20%, an elastic modulus: about 80 MPa). Subsequently, a polyimide precursor solution is coated on the lower stretchable layer, and treated through photolithography to form a stretch controlling layer including 2 μm-thick serpentine-shaped polyimide patterns (an elastic modulus: about 2.5 GPa). A solution prepared by dissolving styrene-ethylene-butylene-styrene (SEBS) (H1043, Asahi Kasei) and a hardener in toluene is coated on the stretch controlling layer, and then dried, cured, and patterned to form a 3 μm-thick upper stretchable layer (a stretching ratio: about 20%, an elastic modulus: about 80 MPa), manufacturing a stretchable device system.

Evaluation II

Figure 17:
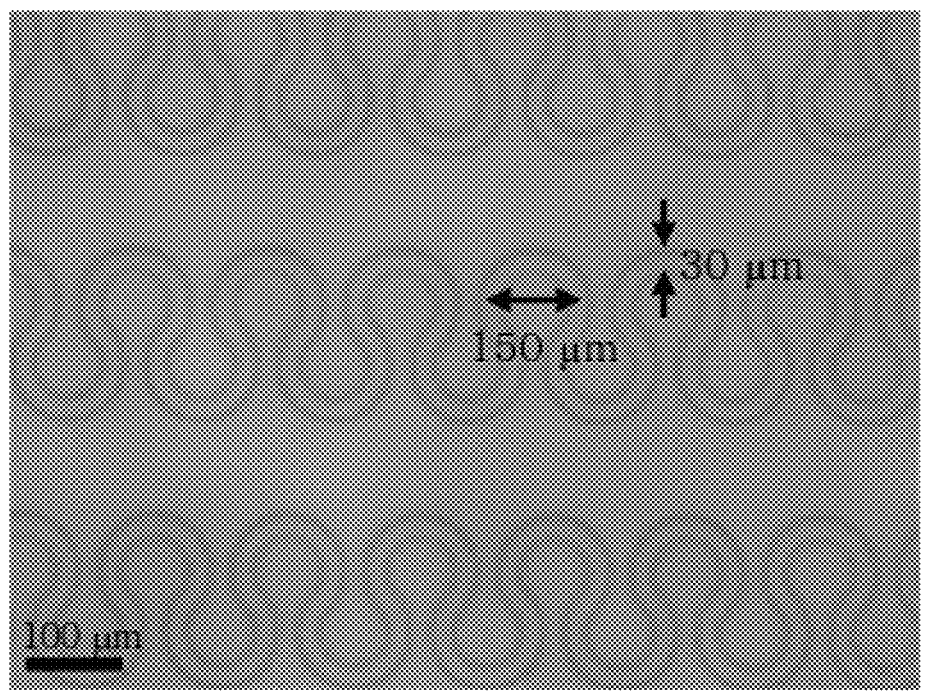
FIG. 17 is an optical micrograph of the stretchable device system according to Example 9.

FIG. 17 is an optical micrograph of the stretchable device system according to Example 9.

Referring to FIG. 17, on the stretchable layer, a stretch controlling layer having a particular (or, alternatively, predetermined) thickness and length is formed.

Manufacture of Stretchable Device System III

Example 10

A stretchable device system is manufactured according to the same method as Example 9 except that a polyethyleneterephthalate (PET) patterns are formed by a transfer method to have a shape shown in FIG. 4A instead of the polyimide patterns.

Example 11

A stretchable device system is manufactured according to the same method as Example 9 except that a polyethyleneterephthalate (PET) patterns are formed by the transfer method to have a shape shown in FIG. 4B instead of the polyimide patterns.

Example 12

A stretchable device system is manufactured according to the same method as Example 9 except that a polyethyleneterephthalate (PET) patterns are formed by the transfer method to have a shape shown in FIG. 4C instead of the polyimide patterns.

EVALUATION III

Figure 18:
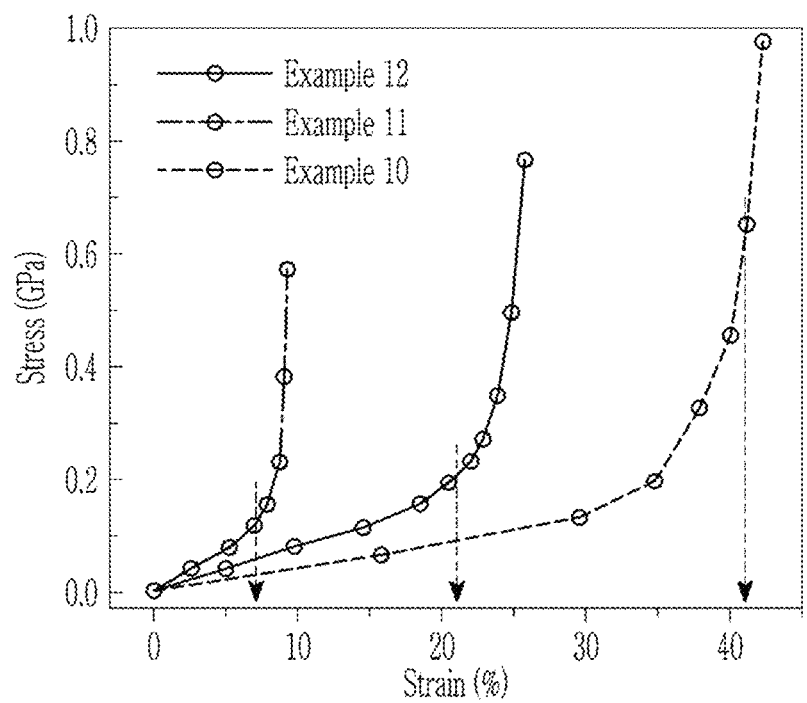
FIG. 18 is a strain-stress graph of the stretchable device system according to Examples 10 to 12.

FIG. 18 is a strain-stress graph of the stretchable device systems according to Examples 10 to 12.

TABLE 2

|  | Geometric maximum strain (%) |
| --- | --- |
| Example 10 | 41 |
| Example 11 | 7 |
| Example 12 | 21 |

Referring to FIG. 18 and Table 2, the stretchable device systems according to Examples 10 to 12 exhibit a sharply increasing strain-stress slope around geometric maximum strain. Accordingly, the stretchable device systems according to Examples 10 to 12 exhibit strain-controlling characteristics.

While the inventive concepts have been described in connection with what is presently considered to be practical example embodiments, it is to be understood that the inventive concepts are not limited to these example embodiments. On the contrary, the inventive concepts are intended to cover various modifications and equivalent arrangements included within the spirit and scope of the appended claims.

What is claimed is:

1. A stretchable device system, comprising:
   a stretchable layer having a first elastic modulus;
   a plurality of unit devices under, inside, or on the stretchable layer;
   a stretch controlling layer being geometrically stretchable, the stretch controlling layer having a second elastic modulus higher than the first elastic modulus; and
   a connecting wire electrically connecting adjacent unit devices of the plurality of unit devices,
   wherein the stretch controlling layer comprises geometric lattice patterns, and
   wherein at least a portion of the stretch controlling layer is overlapped with the connecting wire.

2. The stretchable device system of claim 1, wherein the stretch controlling layer is on, under, or inside the stretchable layer, and the stretch controlling layer is isolated from direct contact with the plurality of unit devices.

3. The stretchable device system of claim 1, wherein the stretch controlling layer comprises patterns connected as a whole.

4. The stretchable device system of claim 1, wherein at least a portion of the stretch controlling layer has a serpentine or zigzag shape.

5. The stretchable device system of claim 1, wherein the stretch controlling layer comprises a polymer.

6. The stretchable device system of claim 1, wherein
   the stretchable layer comprises a first elastomer having the first elastic modulus, and
   the stretch controlling layer comprises a second elastomer having the second elastic modulus or a non-elastomer having the second elastic modulus.

7. The stretchable device system of claim 6, wherein the first elastomer includes
   a copolymer including
      a first structural unit selected from a styrene structural unit, an olefin structural unit, a urethane structural unit, an ether structural unit, and a combination thereof, and
      a second structural unit selected from an ethylene structural unit, a propylene structural unit, a butylene structural unit, an isobutylene structural unit, a butadiene structural unit, an isoprene structural unit, and a combination thereof;
   polyurethane;
   polyorganosiloxane; or
   a combination thereof, and
   the second elastomer or the non-elastomer includes polystyrene, polyolefin, polyimide, polyamideimide, polyethyleneterephthalate, polyethylenenaphthalate, polymethylmethacrylate, polycarbonate, polyethersulfone, or a combination thereof.

8. The stretchable device system of claim 6, wherein the first elastomer and the second elastomer or the non-elastomer comprises at least one same structural unit.

9. The stretchable device system of claim 1, wherein the second elastic modulus is about 10 times to about 1000 times higher than the first elastic modulus.

10. The stretchable device system of claim 1, wherein
    the first elastic modulus is greater than or equal to about $10^2$ Pa and less than about $10^8$ Pa,
    the second elastic modulus is about $10^8$ Pa to about $10^{10}$ Pa, and
    the second elastic modulus is about 10 times higher than the first elastic modulus.

11. The stretchable device system of claim 1, wherein the second elastic modulus is lower than or equal to an elastic modulus of the plurality of unit devices.

12. The stretchable device system of claim 1, wherein the stretchable layer includes
    a stretchable substrate supporting the plurality of unit devices,
    a protective layer or a passivation layer covering the plurality of unit devices, or
    a combination thereof.

13. The stretchable device system of claim 1, wherein each unit device includes a light emitting device, a light absorbing device, a transistor, a resistance device, an imaging device, or a combination thereof.

14. The stretchable device system of claim 1, wherein the stretchable device system is a display panel or a sensor.

15. An electronic device comprising the stretchable device system of claim 1.

16. A stretchable device system, comprising:
a stretchable layer having a first elastic modulus;
a plurality of unit devices under, inside, or on the stretchable layer; and
a stretch controlling layer being geometrically stretchable, the stretch controlling layer having a second elastic modulus higher the first elastic modulus, wherein the stretch controlling layer includes
a plurality of first patterns overlapped with separate, respective unit devices of the plurality of unit devices, and
a second pattern connecting adjacent first patterns of the plurality of first patterns.

17. The stretchable device system of claim 16, wherein each first pattern has a size covering all edges of a separate unit device of the plurality of unit devices.

18. The stretchable device system of claim 16, wherein the second pattern comprises geometric lattice patterns.

19. The stretchable device system of claim 16, wherein the second pattern has a serpentine or zigzag shape.

20. A protective film for a stretchable device system, the protective film comprising:
a stretchable layer including a first elastomer, and
a stretch controlling layer under, on, or inside the stretchable layer, and
the stretch controlling layer including a second elastomer or a non-elastomer having a higher elastic modulus than a separate elastic modulus of the first elastomer,
wherein the stretch controlling layer is geometrically stretchable,
wherein the first elastomer includes
a copolymer including
a first structural unit selected styrene structural unit, an olefin structural unit, a urethane structural unit, an ether structural unit, and a combination thereof, and
a second structural unit selected from an ethylene structural unit, a propylene structural unit, a butylene structural unit, an isobutylene structural unit, a butadiene structural unit, an isoprene structural unit, a and a combination thereof;
polyurethane;
polyorganosiloxane; or
a combination thereof, and
wherein the second elastomer or the non-elastomer includes polystyrene, polyolefin, polyimide, polyamideimide, polyethyleneterephthalate, polyethylenenaphthalate, polymethylmethacrylate, polycarbonate, polyethersulfone, or a combination thereof.

21. The protective film of claim 20, wherein
the stretch controlling layer comprises patterns connected as a whole, and
the patterns comprise geometric lattice patterns, patterns having serpentine or zigzag patterns, or a combination thereof.

* * * * *